US00PP33401P2

(12) United States Plant Patent
Ui

(10) Patent No.: US PP33,401 P2
(45) Date of Patent: Aug. 24, 2021

(54) ***PETUNIA* 'KERSUCAN'**

(50) Latin Name: *Petunia atkinsiana*
Varietal Denomination: KERSUCAN

(71) Applicant: Sakata Ornamentals A/S, Marsley (DK)

(72) Inventor: Akinobu Ui, Kakegawa (JP)

( * ) Notice: Subject to any disclaimer, the term of this patent is extended or adjusted under 35 U.S.C. 154(b) by 0 days.

(21) Appl. No.: 17/104,991

(22) Filed: Nov. 25, 2020

(51) Int. Cl.
*A01H 6/82* (2018.01)
*A01H 5/02* (2018.01)

(52) U.S. Cl.
USPC ..... Plt./356.17

(58) Field of Classification Search
USPC ..... Plt./356.17
See application file for complete search history.

*Primary Examiner* — Annette H Para
(74) *Attorney, Agent, or Firm* — Cassandra Bright

(57) ABSTRACT

A new and distinct *Petunia* cultivar named 'KERSUCAN' is disclosed, characterized by a compact, mounding, growth habit. Plants produce light purple stable double flowers, not producing single flowers under stress. The plants flower freely and begin flowering under short day condition. The new variety is a *Petunia*, normally produced as an outdoor garden or container plant.

2 Drawing Sheets

Figure 1:
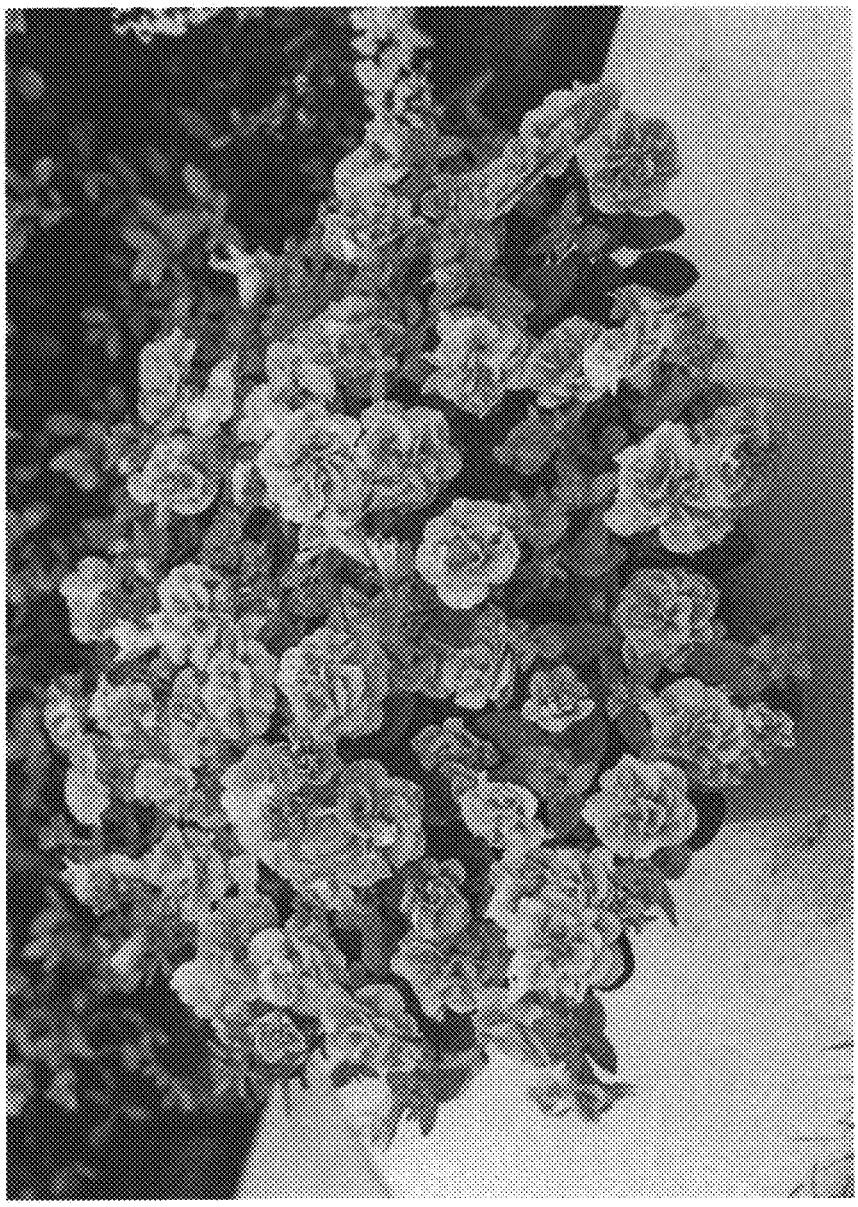

Latin name of the genus and species: *Petunia atkinsiana*.
Variety denomination: 'KERSUCAN'.

BACKGROUND OF THE INVENTION

'KERSUCAN' is a product of a breeding and selection program for ornamental *Petunia* varieties to be vegetatively propagated. The new plant of the present invention comprises a new and distinct cultivar of *Petunia* plant.

'KERSUCAN' is a seedling resulting from the crossing of an unnamed, unpatented proprietary *Petunia atkinsiana* with the pollen parent, a different unpatented, unnamed proprietary, *Petunia atkinsiana*, conducted in August 2015. The selection of the new variety was made in May 2016, by the inventor at a research greenhouse located in Salinas, Calif.

'KERSUCAN' was first asexually reproduced by vegetative terminal cuttings at a research greenhouse in Salinas, Calif., September 2016. The new cultivar has been found to retain its distinctive characteristics through successive asexual propagations.

SUMMARY OF THE INVENTION

The cultivar 'KERSUCAN' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERSUCAN' These characteristics in combination distinguish 'KERSUCAN' as a new and distinct *Petunia* cultivar:

1. Stable double flowers, not becoming single under stress.
2. Short day flowering, flower bud initiation occurs in day lengths of less than 8 hours.
3. Compact, mounding plant habit.

4. Abundant flowering.
5. Light purple flower color.

PARENT COMPARISON

Plants of the new cultivar 'KERSUCAN' are similar to plants of the seed parent in most horticultural characteristics, however, plants of the new cultivar 'KERSUCAN' differ in the following:

1. 'KERSUCAN' has a compact, mounded plant habit, the seed parent is more spreading and larger.
2. The new variety produces double flowers; the seed parent produces single flowers.

Plants of the new cultivar 'KERSUCAN' are similar to plants of the pollen parent in most horticultural characteristics however, plants of the new cultivar 'KERSUCAN' differ in the following:

1. 'KERSUCAN' has a different flower color than the pollen parent.

COMMERCIAL COMPARISON

Plants of the new cultivar 'KERSUCAN' can be compared to the commercial variety *Petunia* 'Kirimaji Double Pink Vein', U.S. Plant Pat. No. 13,398. These varieties are similar in most horticultural characteristics. The new variety 'KERSUCAN', however, differs in the following:

1. 'KERSUCAN' has significantly less prominent vein coloration in the flower.
2. 'KERSUCAN' has a compact mounded plant habit, this comparator has a spreading, trailing plant habit.
3. 'KERSUCAN' flowers under shorter day conditions.
4. 'KERSUCAN' has shorter stems.

Plants of the new cultivar 'KERSUCAN' can also be compared to the commercial variety *Petunia* 'Tumbelina Joanna', unpatented. These varieties are similar in most horticultural characteristics, both having double flowers. 'KERSUCAN' however, differs in the following:

1. 'KERSUCAN' has a more compact and mounding habit, this comparator has a spreading habit.
2. 'KERSUCAN' produces smaller flowers.
3. This comparator has a lighter pink flower rim not found in the new variety.

BRIEF DESCRIPTION OF THE PHOTOGRAPHS

The accompanying photograph in FIG. 1 illustrates in full color a typical plant of 'KERSUCAN' grown in a greenhouse, in Cambridge, United Kingdom.

Figure 2:
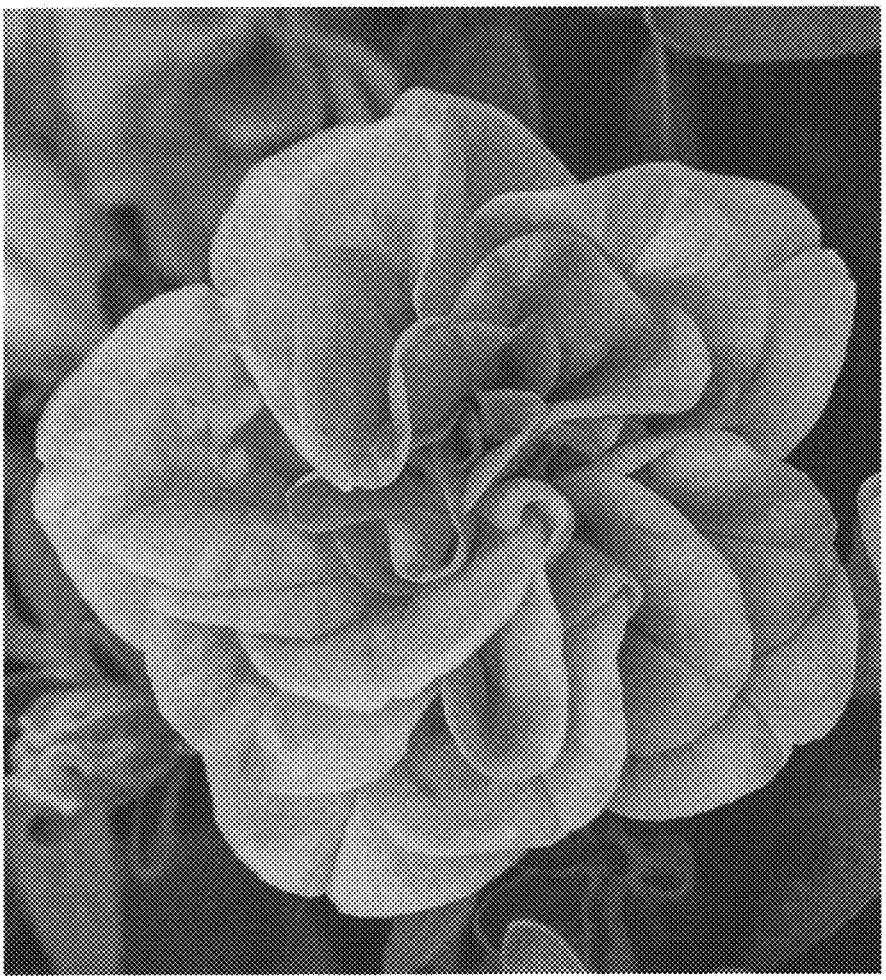

FIG. 2 illustrates in full color a typical mature flower of 'KERSUCAN' during Spring. Age of the plant photographed is approximately 90 days from a rooted cutting in a 20 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'KERSUCAN' plants grown in greenhouse in Cambridge, United Kingdom, under natural lighting. The plants were approximately 10 weeks old from a rooted cutting in a 1.5 liter pot. The growing temperature ranged from 20° C. to 35° C. during the days, 17° C. to 23° C. during the nights. Measurements and numerical values represent averages of typical plant types.

Botanical classification: *Petunia atkinsiana* 'KERSUCAN'.

PROPAGATION

Time to initiate roots: Approximately 10 days at 20° C.

Root description: Fibrous, freely branching. White, to light tan, not accurately measured with R.H.S. chart.

Time to produce a rooted cutting: About 21 to 28 days.

PLANT

Growth habit: Compact, mounded.

Pot size of plant described: 1.5 liter.

Height: 20.3 cm to top of flowering plane.

Plant spread: 32.3 cm.

Growth rate: Moderate.

Length of primary lateral branches: 21.7 cm.

Diameter of lateral branches: 0.4 cm.

Quantity of primary lateral branches: 4.

Characteristics of primary lateral branches:

- *Color.*—Young stem: RHS Yellow-Green 144A. Mature stem: RHS Yellow-Green 146C.
- *Texture.*—Densely pubescent.
- *Strength.*—Strong.

Internode length: 3.23 cm.

FOLIAGE

Leaf:

- *Arrangement.*—Alternate before flowering, then opposite.
- *Form.*—Simple.
- *Quantity.*—19 per main branch.
- *Average length.*—5.0 cm.
- *Average width.*—3.8 cm.
- *Shape of blade.*—Ovate. Oldest foliage closer to elliptic.
- *Apex.*—Acute.
- *Base.*—Attenuate.
- *Margin.*—Entire.
- *Angle of attachment.*—About 45 degrees from stem.
- *Texture of top surface.*—Pubescent.
- *Texture of bottom surface.*—Pubescent.
- *Color.*—Young foliage upper side: RHS Yellow-Green 146A. Young foliage under side: RHS Yellow-Green 146B. Mature foliage upper side: RHS Green N137C. Mature foliage under side: RHS Yellow-Green 146B.
- *Venation.*—Type: Pinnate. Venation color upper side: RHS Yellow-Green 144A. Venation color under side: RHS Yellow-Green 146C.
- *Petiole.*—Length: 0.5 cm. Diameter: 0.3 cm. Color: RHS Yellow-Green 146B. Texture: Pubescent.

FLOWER

Natural flowering season: Spring and Summer in Cambridge, United Kingdom.

Days to flowering from rooted cutting: 21 to 28 days.

Flower type and habit: Double, salverform upward and outwardly facing.

Rate of flower opening: Typically about 2 days from bud to fully opened flower.

Flower longevity on plant: 9 to 10 days.

Approximate quantity of flowers per plant: Average 12 flowers and 12 buds on a plant of this age.

Persistent or self-cleaning: Self-cleaning.

Bud:

- *Shape.*—Conical.
- *Length.*—2.9 cm.
- *Diameter at apex.*—1.4 cm.
- *Diameter at base.*—0.6 cm.
- *Texture.*—Pubescent, more densely pubescent at base.
- *Color.*—RHS Purple N75C. Base/outer tube Yellow-Green 146C.

Flower size:

- *Diameter.*—6 cm.
- *Length.*—*About* 2.5 cm.
- *Flower tube diameter at distal end.*—About 1.9 cm.
- *Flower tube diameter at proximal end.*—About 0.4 cm.

Petals:

- *Length from tube.*—2.3 cm.
- *Length of free portion.*—1.6 cm.
- *Width.*—2.5 cm.
- *Quantity.*—23.
- *Shape.*—Cuneate.
- *Appearance.*—Matte.
- *Texture, upper surface.*—Glabrous.
- *Texture, lower surface.*—Sparsely pubescent.
- *Apex.*—Obtuse.
- *Margin.*—Entire, undulating to ruffled.
- *Lobing.*—Very weak to absent.

Color:

- *When opening.*—
- *Upper surface.*—Innermost petals near Purple N75. Petals in exterior whorls near Purple 76A.
- *Lower surface.*—Near Purple 76C.

*Fully opened.*—

*Upper surface.*—Near Purple N75C with central flush near N75A.

*Lower surface.*—Near Purple 76D with slight flush of 76C.

*Flower throat (inside).*—RHS Yellow-Green 145C.

*Flower throat, vein.*—RHS Yellow-Green 145B.

*Flower tube (outside).*—RHS Yellow-Green 145C.

*Flower tube, vein (outside).*—RHS Yellow-Green 146D.

Corolla tube:

*Length.*—2.5 cm.

*Diameter at distal end.*—1.9 cm.

*Diameter at proximal end.*—0.4 cm.

*Texture, inner surface.*—Glabrous.

*Texture, outer surface.*—Pubescent.

Sepals:

*Quantity per flower.*—5 fused along lower half.

*Shape.*—Cuneate.

*Length.*—2.0 cm.

*Width.*—0.5 cm.

*Margin.*—Entire.

*Apex.*—Acute, occasionally obtuse.

*Texture, lower surfaces.*—Pubescent.

*Texture, upper surfaces.*—Pubescent.

*Color.*—Upper Surface: Between RHS Green N137B. Lower Surface: RHS Yellow-Green 146A.

Peduncle:

*Strength.*—Strong.

*Aspect.*—About 60 degrees to stem.

*Length.*—3.0 cm.

*Diameter.*—3 mm.

*Texture.*—Pubescent.

*Color.*—Near RHS Yellow-Green 144A.

Fragrance: None.

REPRODUCTIVE ORGANS

Stamens: None observed.

Pistil: None observed.

OTHER CHARACTERISTICS

Seeds and fruits: Not observed to date.

Disease/pest resistance: Neither resistance nor susceptibility to the normal diseases and pests of *Petunia* have been observed. Typical well-known diseases include: *Botrytis cineria, Fusarium, Pythium, Phytophthora*, and *Rhizoctonia* species. Typical well-known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'KERSUCAN' as herein illustrated and described.

* * * * *